(12) United States Patent
Kajiro

(10) Patent No.: US 6,424,461 B1
(45) Date of Patent: Jul. 23, 2002

(54) APPARATUS FOR OBSERVING INTERIOR FROM AN ULTRAMICROPORE SPACE

(75) Inventor: Yoichi Kajiro, Tokyo (JP)

(73) Assignee: Hirox Co., Ltd. (JP)

( * ) Notice: Subject to any disclaimer, the term of this patent is extended or adjusted under 35 U.S.C. 154(b) by 0 days.

(21) Appl. No.: 09/639,459

(22) Filed: Aug. 15, 2000

(30) Foreign Application Priority Data

Mar. 10, 2000 (JP) ....................................... 2000-066599

(51) Int. Cl.⁷ .............................................. G02B 21/06
(52) U.S. Cl. ........................ 359/385; 359/390; 359/798
(58) Field of Search ................................ 359/368, 381, 359/385, 387, 388, 389, 390, 726, 798

(56) References Cited

U.S. PATENT DOCUMENTS 3,971,621 A * 7/1976 Albrecht-Buehler ........ 359/390
4,657,357 A * 4/1987 Nishimura et al. .......... 359/377
4,963,021 A * 10/1990 Nakamura et al. .......... 356/153
5,249,077 A * 9/1993 Laronga et al. ............. 359/385

FOREIGN PATENT DOCUMENTS

DE 198 47 913 A1 5/1999

* cited by examiner

Primary Examiner—Mark A. Robinson
(74) Attorney, Agent, or Firm—McGlew and Tuttle, P.C.

(57) ABSTRACT

An apparatus for an object in an ultramicropore space has a lens system so that an incidence point P with the diameter in a range from 0.3 to 0.7 mm comes to a position in a range of 12 to 17 mm away from the front side of an object lens 30. At the same time a reflection mirror 15 is positioned with a reflection mirror mounting member 8 formed with the V-shaped form in front of the object lens 30 and a reflection mirror holding frame 8 at the position of the incidence point. This arrangement is useful fir example to observe a soldered section 52 of an IC chip 50 by inserting this reflection mirror 15 into the ultramicropore space.

2 Claims, 6 Drawing Sheets

APPARATUS FOR OBSERVING INTERIOR FROM AN ULTRAMICROPORE SPACE

FIELD OF THE INVENTION

The present invention relates to an apparatus for observing, for instance, situations of an IC soldered to a printed board with an ultra-small close-up photographing device. More particularly, this invention relates to an apparatus which can be used for not only simply observing an object in an ultramicropore, but also for observing an object in an ultramicropore from various angles by inserting a reflection mirror into the ultramicropore.

BACKGROUND OF THE INVENTION

An apparatus for observing situations of an IC soldered on a print-circuit board with a ultra-small close-up photographing device is disclosed in German Patent DE 19847913A1. This known apparatus comprises an eyepiece unit (3), an object glass head (2), an image transfer unit (4) for transferring an image photographed by the object glass head (2) to the eyepiece unit (3), and lighting units (15, 1) for illuminating a soldering joint (21) to be checked. The device disclosed is especially in an apparatus for optically checking electric parts arranged on a surface of a print-circuit board (19) or a soldering joint out of sight between electric parts (20) and the print-circuit board (19). The object glass head (2) has a unit (9) for deflecting an image, and the unit extends up to an outer edge of the object glass head (2) in the axial direction. In this apparatus, the lighting units (15, 16) are relatively positioned against the object glass head (2) so that an exit angle of light projected from the lighting units and also transferred through the object glass head (2) is basically equal to a deflection angle caused by the image deflection unit (9) and at the same time the light exit is provided at or near an outer edge of the object glass head (2) adjacent to the image deflection unit (9) in its axial direction.

In the observation apparatus having the configuration as described above, however, as the object glass head (2) approaches a soldered IC during observation, when the IC is arranged singly on a surface of a print-circuit board and there is nothing around the IC, observation is possible. However, if any other IC or other electric parts is provided on the print-circuit board in vicinity to the IC (like in most practical cases), it is impossible to insert the object glass head (2) into a space with the width of only several millimeters between the IC and other parts. In the case as described above, there is no way but to observe the soldering situation of the IC from the diagonal direction keeping the object glass head (2) a little away from the space, so that it is impossible to completely observe the situations of the soldered IC and therefore the result of the observation is not sufficient.

The publication also include descriptions concerning a lighting unit, but the light exit of this lighting unit is provided at or near an outer edge of the object glass head (2) adjacent to the image deflection unit (9) in its axial direction, so that the size of the object glass head (2) is disadvantageously larger.

Further the publication also discloses a light reflection head (23) for illuminating an object to be observed from its behind, but when a silhouette of the observed object being illuminated from its behind, an object positioned inside (or behind) the silhouette cannot be observed.

In the example disclosed in the publication, when it is desired to replace the object glass head (2) with a new one well adapted for observation of an object to be observed, or when the object glass head (2) is damaged, the object glass head (2) can not easily be exchanged with another one or a new one.

In the example disclosed in the publication, a polarizing prism (9) or a polarizing mirror is used to observe an object from the horizontal direction, but if the polarizing prism (9) or polarizing mirror is assembled with low precision due to a small mistake, inaccuracy occurs in polarization and fine adjustment is required, and to evade the troubles as described above, excellent technique and expertise are required in assembling the component.

SUMMARY AND OBJECTS OF THE INVENTION

The present invention has been proposed to overcome the problems as described above, and a first object of the present invention is to provide an apparatus enabling observation of an object in a ultramicropore space.

A second object of the present invention is to provide an apparatus enabling observation of an object in a ultramicropore space by inserting the apparatus in the pore space (between components).

A third object of the present invention is to make it possible to exchange a reflection mirror with another one having the different size or to exchange a reflection mirror, when broken, with a new one.

A fourth object of the present invention is to make it possible to completely observe an object from any angle by illuminating the object at various angles.

A fifth object of the present invention is to give a some degree of allowance in assembly of a reflection mirror so that the component can be assembled by any person not sufficiently experienced in the art.

According to the invention, an apparatus is provided for observing inside of an objection to be observed from a ultramicropore space thereon. In a front side of an object glass, a reflection mirror mounting member spans over a center of the object glass having a flat form. The reflection mirror mounting member projects from right and left. A reflection mirror is mounted at a tip of this reflection mirror mounting member.

A reflection mirror with the size suited to an object to be observed is mounted on a reflection mirror mounting member, and the reflection mirror is faced against a soldering section by bringing the reflection mirror mounting member close to, for instance, a periphery of an IC as an object to be observed on a print-circuit board.

The light for illumination from a light source goes through a bundle of optical fibers and divides to two portions, each of which passes through an optical fiber in the reflection mirror mounting member and further through a reflection mirror holding frame and is projected to the reflection mirror from the light-outgoing edge, and then the light beam is reflected on the reflection mirror, changes its direction by 90 degrees, and illuminates the soldering section.

An image of the soldering section illuminated as described above is refracted by 90 degrees on the reflection mirror, the image light passes along a light axis of the lens system, passes through and is focused by a group of object glasses, a group of internal lenses inside the mirror cylinder, and a group of relay lenses. The focused image is photographed by an ultra small close-up photographing unit and displayed, for instance, on a monitor screen.

It is to be noted that the configuration is also allowable in which a reflection mirror for reflecting the illumination light is not used and light-outgoing edges (illumination heads) of optical fibers are located at any positions around an object to be observed so that the object is illuminated at any angles or from any directions.

When it is desired to observe the soldering section from a different direction, or when an angle of the reflection mirror is not appropriate, any desired correction window at a different range from a light axis of the optical system in the radial direction is selected by driving a reflection mirror angle correction unit incorporated in the optical system to control the incoming light for adjustment.

When the reflection mirror holding frame can be removed from the reflection mirror mounting member, any reflection mirror with the size and angle suited to an object to be observed can freely be selected for use, and in addition the reflection mirror can easily be replaced, when damaged, with a new one.

When inside of a soldered section of an IC is complicated and can not fully be illuminated by the illumination light, illumination heads of optical fibers are unloosened from the bundle and inserted into an ultramicropore space respectively. In that case, as the optical fibers are separated from each other, the illumination heads can enter the inside through the micropore space, and illuminate an area therearound. As the result, by using the illuminating unit with separated illumination heads, it is possible to observe inside of a soldering section which can not be observed with the conventional illuminating unit.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENTS

Figure 1:
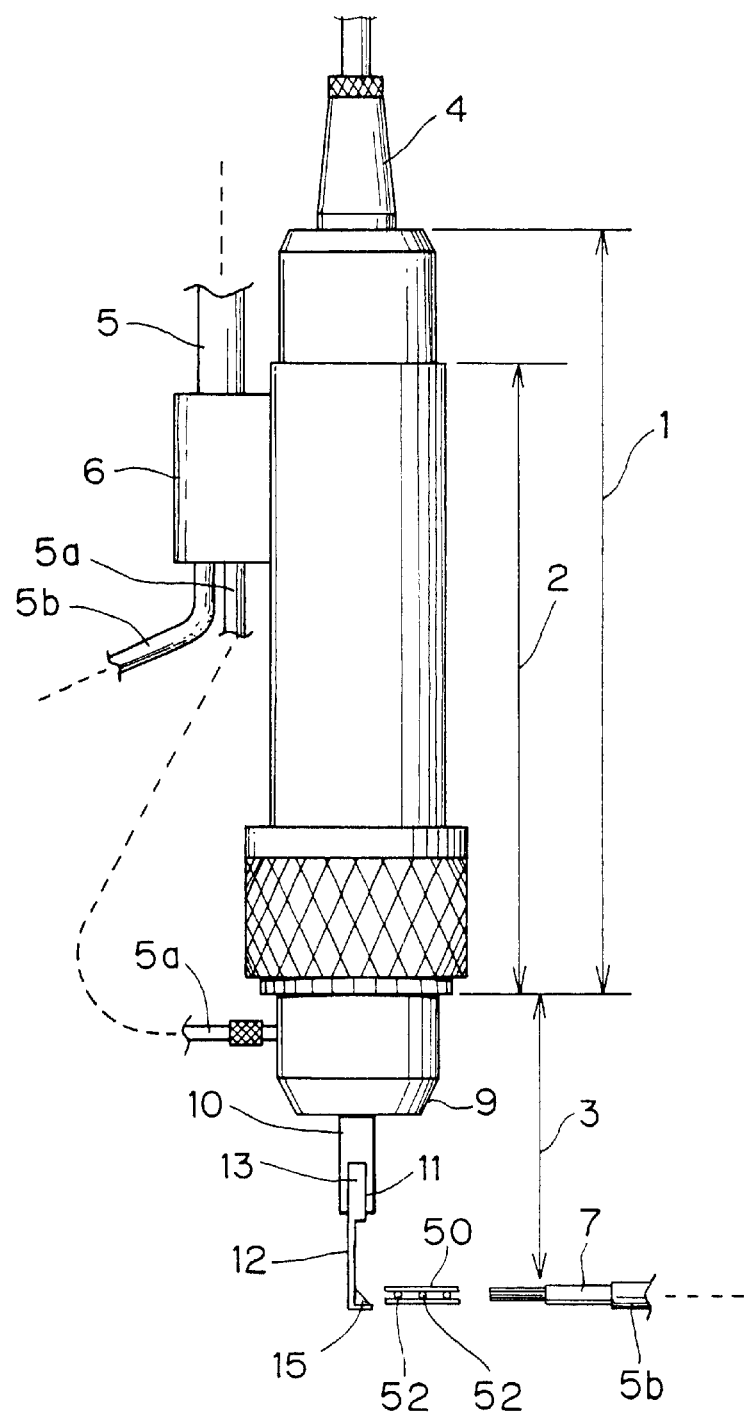
FIG. 1 is an explanatory veiw showing appearance of an observation apparatus.

Referring to the drawings in particular, the present invention provides an observation apparatus used for observing a soldered section of an IC mounted on a print-circuit board or the like, and the observation apparatus is especially useful when observing the inside from a micropore space with the diameter of 1.5 mm or below often described as ultramicropore space. Generally observation is made from the normal or diagonal direction, but an object can be viewed also from the front side when the mirror is removed.

Designing of an optical system using lenses therein is generally made on the presumption that inside of an object is observed with the optical system from an ultramicropore space thereof, an incidence point or incidence point is positioned in front of the object lens (object lens) in a range from 7 to 17 mm therefrom. Further, a diameter of the incidence point in a range from 0.3 to 0.7 mm is effective to accommodate varieties of objects for observation. When the incidence point is located at a position less than 7 mm away from the optical system, there are many restrictions in mounting the reflection mirror, and when the distance is 17 mm or more, the apparatus is inconvenient in practical use. This inconvenience depends on form and size of an object to be observed, however, so that the distance from 5 to 32 mm is within the technical range of the present invention. The reflection mirror can be minimized at the position of the incidence point, but the reflection mirror may be displaced a little forward or backward from the position of the incidence point.

By designing the optical system as described above, a clear image of inside of an ultramicropore space can be obtained, and especially by setting a diameter of the incidence point in a range from 0.3 mm to 0.7 mm, the size of reflection mirror can be minimized. Reduction in size of the reflection mirror makes it possible to observe the soldering situation or the like from the side or from the diagonal direction by inserting the reflection mirror into an ultramicropore space in which a chip or the like is provided, which is the greatest feature of the present invention. It is to be noted that, when practically allowable, the range from 0.2 to 2 mm is within the technical range of the present invention.

The light for illumination is introduced from the light source via optical fibers (a bundle thereof) into the observation apparatus. This bundle of optical fibers is divided to two portions in the reflection mirror mounting member with the light irradiated from the illumination head of each optical fiber, and the outgoing light beam is reflected on the reflection mirror and illuminates an object to be observed. Although the illumination is generally made in the same direction as that for observation (namely, the direction of light axis), an illumination head of each optical fiber may be located at any position around the object for observation according to the necessity, for instance, to illuminate the object from its behind, or to send the illumination light to inside of a component which can not be illuminated in the conventional technology by separating the bundled optical fibers from each other and inserting each optical fiber into an ultramicropore space on the component.

Embodiment 1

Figure 2:
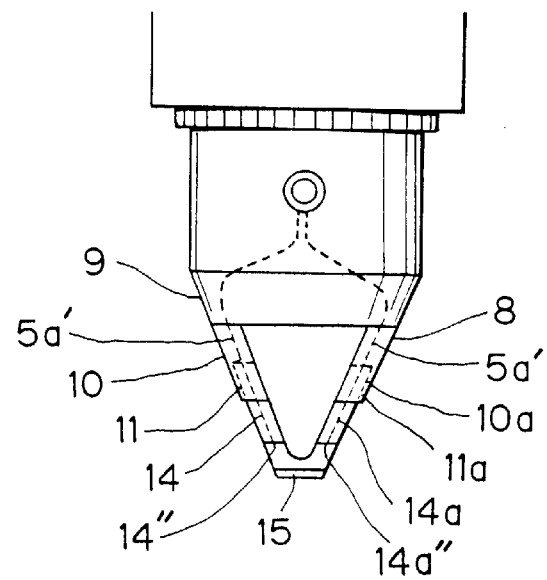
FIG. 2 is a side view of an observation head.
Figure 3:
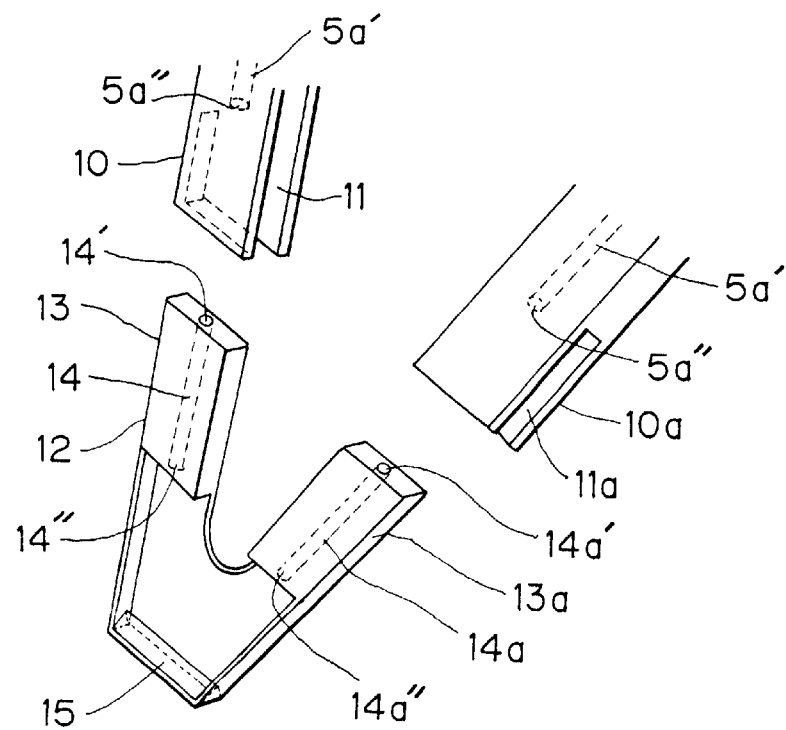
FIG. 3 is an explanatory view showing a reflection mirror (a holding frame) and a section in which the reflection mirror is set.
Figure 4:
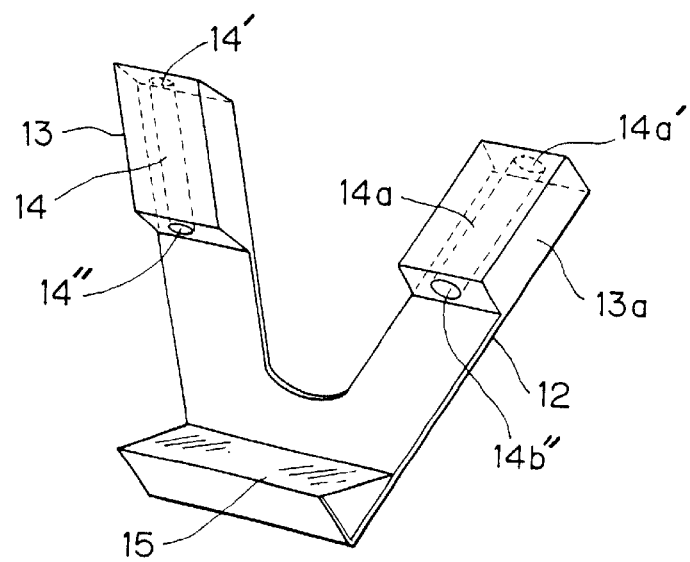
FIG. 4 is an explanatory view of the reflection mirror.
Figure 5:
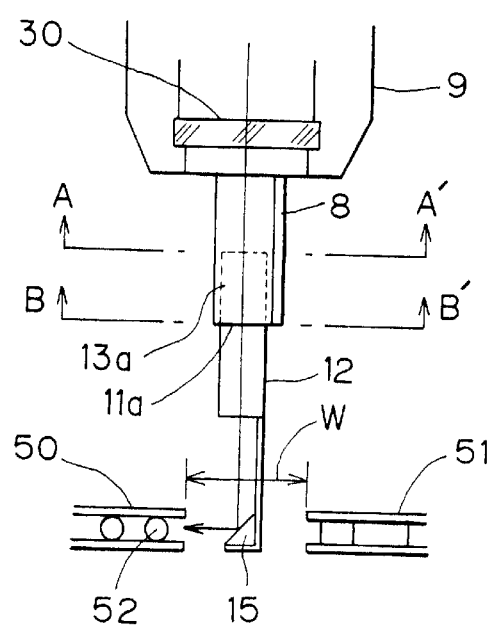
FIG. 5 is a cross-sectional view of a reflection mirror mounting member section.
Figure 6:
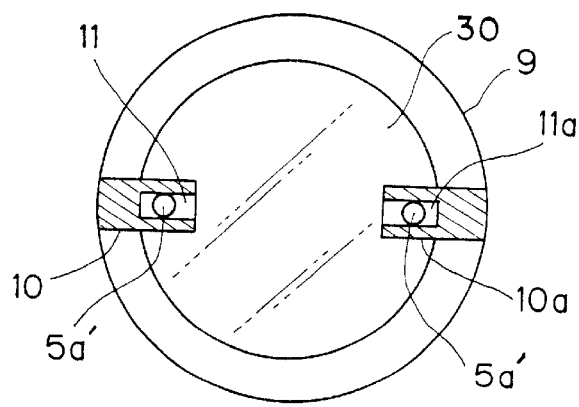
FIG. 6 is a cross-sectional view taken along the line A–A' in FIG. 5.
Figure 7:
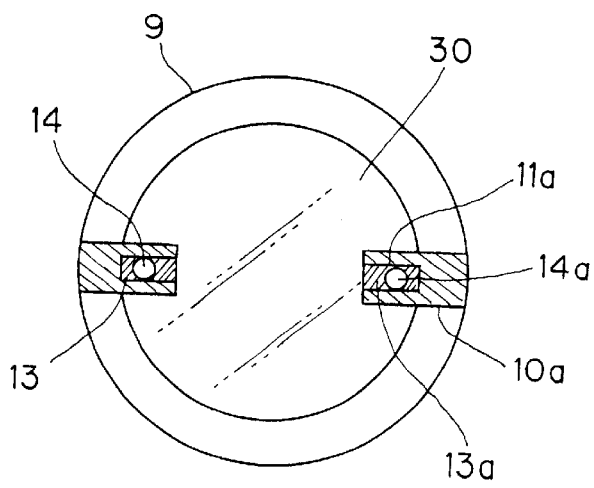
FIG. 7 is a cross-sectional view taken along the line B–B' in FIG. 5.

FIG. 1 is an explanatory view showing appearance of the observation apparatus as a whole, FIG. 2 is a side view showing an observation head section, FIG. 3 is an explanatory view showing a reflection mirror and a section which the reflection mirror is mounted on or dismounted from, FIG. 4 is an explanatory view for the reflection mirror, FIG. 5 is a cross-sectional view of the reflection mirror mounting member, FIG. 6 is a cross-sectional view of the reflection mirror mounting member taken along the line A–A' in FIG. 5, and FIG. 7 is a cross-sectional view of the reflection mirror mounting member taken along the line B–B' in FIG. 5.

In FIGS. 1 to 7, the reference numeral 1 indicates a basic body of the observation apparatus, and the basic body of the observation apparatus 1 is held on a control table, and can freely change its position by moving up and down or by turning. Also in the FIGS. 1 to 7, designated at the reference numeral 2 is a mirror cylinder section of the basic body 1, at 3 is an observation head section, at 4 an ultra-small close-up photographing unit (CCD camera), and at 5 is a bundle of optical fiber cables for illumination extending from the light source. This optical fiber cable 5 is divided to cables 5a, 5b at a connector 6, and the cable 5a enters the observation head 3, while the other cable extends up to a backlight illumination head 7.

Further in FIGS. 1 to 7, the reference numeral 8 indicates a reflection mirror mounting member formed on a mount 9 for a group of object lenses 30, and this reflection mirror mounting member 8 has flat leg bodies 10, 10a projecting right and left from a center of the object lens group 30 in the V form, and slits 11, 11a in which the reflection mirror holding frame described hereinafter are formed in the lower section (at a tip) thereof. A light-outgoing edge 5a" of the optical fiber cable 5a is provided at the depth of each of slits 11, 11a of the two leg bodies 10, 10a.

The reference numeral 12 indicates a flat reflection mirror holding frame having the V-shaped general form, and upper edges 13, 13a of this reflection mirror frame 12 detachably engages the slits 11, 11a of the leg bodies 10, 10a, and in the upper edges 13, 13a, light-incoming edges 14', 14a'face against the light-outgoing edge 5a" of the optical fiber cable 5a in each of the leg bodies 10, 10a are provided, and optically conductive flat prisms 14, 14a having the light-outgoing edges 14", 14a" facing against the reflection mirror 15 respectively are incorporated therein. The optically conductive prisms 14, 14a may be optical fibers.

Figure 8:
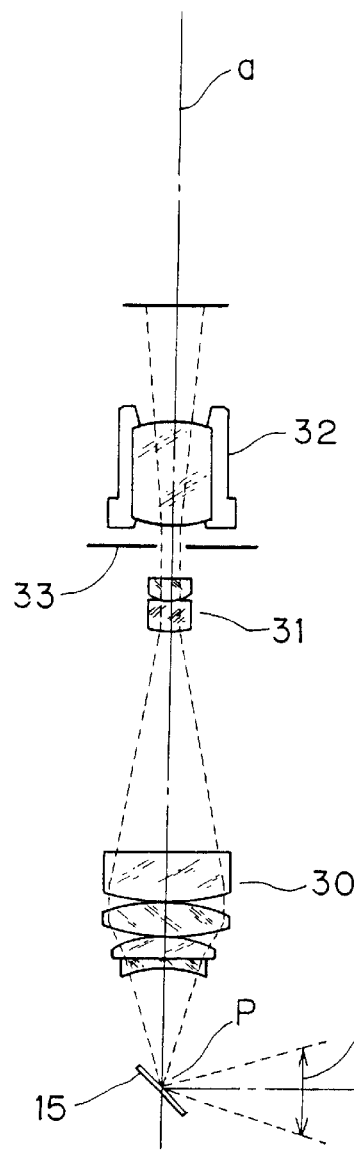
FIG. 8 is an explanatory view showing an optical system.

The reflection mirror 15 refracts a direction of a light beam by 90 degrees against the reflection mirror holding frame 12, and although prisms are used in this embodiment, the configuration is allowable in which a direction of the light beam is changed by 90 degrees by a flat mirror set in a 45-degree inclined posture, and the term of "reflection mirror" as defined herein indicates both a prism and a flat mirror. The optical system in this embodiment is described below with reference to FIG. 8. In FIG. 8, each lens group comprises an object lens group 30 having a positive focus range and comprising several pieces of convex and concave lenses; an inner lens group 31 located at the back of the object lens group 30, having a positive focus range and comprising a convex lens and a concave lens; and a relay lens group 32 having a positive focus range and comprising several pieces of lenses, and the lens groups are designed so that incidence points P each having the diameter of 0.5 mm are formed at the position 10 mm away from the object lens group 30, and the reflection mirror 15 refracts the light axis a by 90 degrees at the position of this incidence point P.

Figure 9:
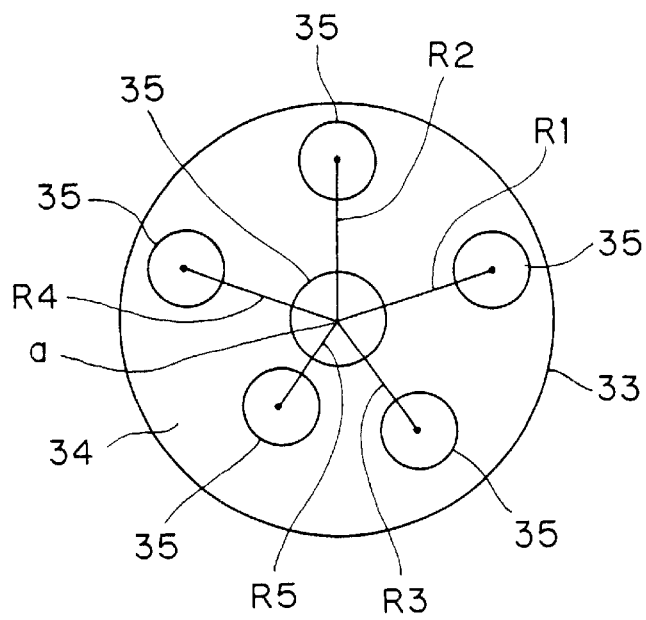
FIG. 9 is an explanatory view showing a reflection mirror angle correction unit.

The reference numeral 33 indicates a mirror angle correction unit provided between the internal lens group 31 and relay lens group 32, and this correction unit 33 has correction windows 35 ••• formed at different positions $R_1, R_2, R_3, R_4, R_5$, in the radial direction around a center (light axis a) of turning disk 34 as shown in FIG. 9, and by selecting any of the windows 35 •••, it is possible to select an incident light beam for changing an angle for observation or to correct a reflection angle of the reflection mirror 15.

In the embodiment, when focusing on an object A in front of the object lens group 30, those to be kept open are selected from the windows 35 of the correction unit 33 with other windows closed, and the internal lens group 31 and relay lens group 32 are simultaneously moved forward along the light axis a with the correction unit 33 fixed. As the result, it is possible to perform focusing in a range from a position just ahead the incidence point P to a position about 10 or more millimeters away from the incidence point P. An aperture diameter of the windows of the correction unit 33 in this embodiment is fixed, but the diameter may be variable.

A situation in observation of an IC mounted on a print-circuit board with the observation apparatus according to the embodiment is shown in FIG. 1 and FIG. 5. In this case, a reflection mirror 15 of the observation head 3 is inserted into a space W between IC chips 50 and 51 to observe a state of soldering section 52 in the space from side direction, and the illumination light passes through the optical fibers 5, 5a and then the optical fiber cable 5a' in the reflection mirror mounting member 8, and is irradiated from the light-outgoing edges 14", 14a" of the flat prisms 14, 14a of the reflection mirror holding frame 12 and reflected on the reflection mirror 15, and then illuminates the soldering section 52.

Embodiment 2

Figure 10:
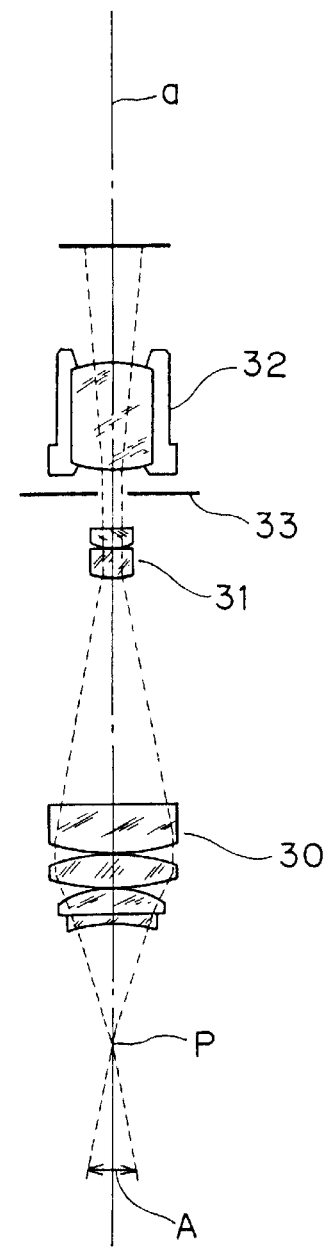
FIG. 10 is an explanatory view showing an optical system in which a reflection mirror is not used.

In Embodiment 1, the reflection mirror 15 is located at the position of the incidence point P, but in the case shown in FIG. 10, the reflection mirror 15 is not used, and the observation head 3 is directly faced to an object for observation. The configuration according to this embodiment is the same as that in Embodiment 1 excluding the point that the reflection mirror 15 is not provided.

Embodiment 3

Figure 11:
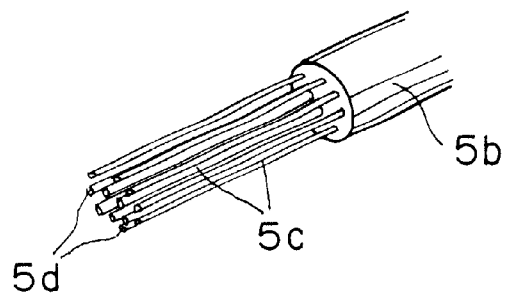
FIG. 11 is an explanatory view showing a situation in which light-outgoing edges of optical fibers are exposed.
Figure 12A:
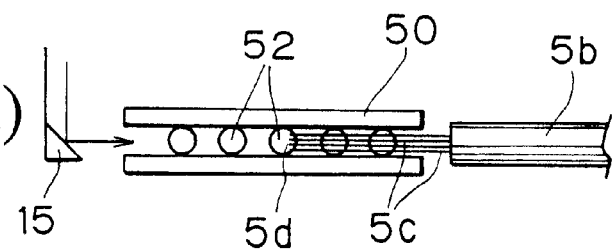
FIG. 12 is an explanatory view showing how the light-outgoing edges of the lighting unit are used.
Figure 12B:
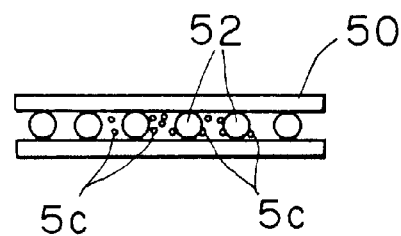
Figure 12C:
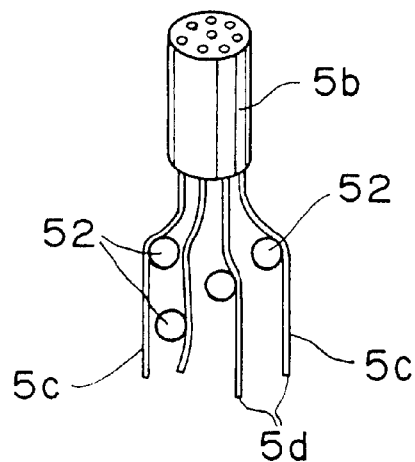

In this embodiment, the optical fiber cable 5 is divided to two portions at the position of connector 6, a tip of one (5b) of the two divided cables is made free, the optical fibers constituting the cable 5b are separated from each other at the free edge as shown in FIG. 11, and tips of the separated fiber cables are inserted into the object for observation 52 as shown in FIG. 12A to FIG. 12C, and thus even a section which otherwise is not illuminated can be observed by inserting the light-outgoing edge 5d of the optical fiber 5c into inside of the object from an ultramicropore space.

Effects of the Invention

As described above, in the optical system according to the present invention, a position of the incidence point is set in a range of 7 to 17 mm in the forward direction away from the object lens, and further a diameter of the incidence point is set in a range from 0.3 to 0.7 mm, so that an object in an ultramicropore space can be observed by placing the reflection mirror at the position of or near the incidence point. As a diameter of the incidence point is small, the size of the reflection mirror can be minimized, and further as the reflection mirror holding frame is flat, observation can be performed by inserting the reflection mirror into an ultra-micropore space.

As the reflection mirror can easily be replaced with another one, a reflection mirror with the appropriate size can be selected according to an object for observation, and when a reflection mirror in use is damaged, it can easily be replaced with the spare.

When an angle of the reflection mirror is incorrect, or when it is desired to change an angle for observation, angle adjustment or correction of an error in assembly can be performed by using the reflection mirror angle correction unit, so that excellent technique or expertise is not required in assembling the reflection mirror with high accuracy, and further as the angle for observation can freely be changed according to the necessity, the apparatus is very convenient in practical use.

Further as optical fibers constituting the optical fiber cable can be separated from each other at the light-outgoing edge, even a section to which the illumination light does not reach in the conventional technology can be observed by inserting the separated optical fibers into the ultramicropore spare.

While specific embodiments of the invention have been shown and described in detail to illustrate the application of the principles of the invention, it will be understood that the invention may be embodied otherwise without departing from such principles.

What is claimed is:

1. An apparatus for observing inside of an object to be observed from an ultramicropore space thereon, the apparatus comprising:

an object lens with a front side;

a reflection mirror mounting member spanning over a center of the object lens, the reflection mirror mounting member having a flat form and projecting from right and left; and a reflection mirror mounted at a tip of this reflection mirror mounting member; and optical fibers constituting an optical fiber cable extending from a light source wherein an object for observation in an ultramicropore space can fully be illuminated by separating the optical fibers from each other at a distance from the tip of the cable, inserting tips of the separated optical fibers into the ultramicropore space and then thrusting the optical fibers deep into the ultramicropore space to irradiate the ultramicropore space with the illumination light.

2. The apparatus according to claim 1, wherein a position for illumination can freely be set by manually inserting tips of optical fibers for illumination into an ultramicropore space.

* * * * *